US005773229A

United States Patent [19]
Cone et al.

[11] Patent Number: 5,773,229
[45] Date of Patent: Jun. 30, 1998

[54] MAMMALIAN ADRENOCORTICOTROPIC HORMONE RECEPTORS AND USES

[75] Inventors: Roger D. Cone, Oregon City; Kathleen G. Mountjoy, Portland, both of Oreg.

[73] Assignee: State of Oregon, Portland, Oreg.

[21] Appl. No.: 478,992

[22] Filed: Jun. 7, 1995

Related U.S. Application Data

[62] Division of Ser. No. 77,673, Jun. 15, 1993, Pat. No. 5,554,729, which is a division of Ser. No. 866,560, Apr. 10, 1992, Pat. No. 5,280,112.

[51] Int. Cl.$^6$ ............................................. G01N 33/567
[52] U.S. Cl. .......................... 435/7.21; 435/7.93; 436/503
[58] Field of Search ................................. 435/7.1, 7.21, 435/7.93; 436/503

[56] References Cited

PUBLICATIONS

Burch, R.M. (1991) J. Recept. Res. vol. 11(1–4):101–113.
Hanneman et al., 1987, "Peptides encoded by the pro-opiomelanocortin gene", in *Peptide Hormone as Prohormones*, G. Martinez, ed. (Ellis Horwood Ltd.: Chichester, UK) pp. 53–82.
DeWied & Jolles, 1982, "Neuropeptides derived from pro–opiocortin: Behavioral, physiological and neurochemical effects", Physiol. Rev. 62: 976–1059.
Oelofsen & Ramachandran, 1983, "Studies of corticotropin receptor on rat adipocytes", Arch. Biochem. Biophys. 225: 414–421.

Mertz & Catt, 1991, "Adrenocorticotropin receptors: Functional expression from rat adrenal mRNA in *Xenopus laevis* oocytes", Proc. Natl. Acad. Sci. USA 88:8525–8529.

Moore et al., 1991, "Allgrove syndrome: an autosomal recessive syndrome of ACTH insensitivity, achalasia and alacrima", Endocrinology 34: 107–114.

*Primary Examiner*—Christina Y. Chan
*Assistant Examiner*—Emma Cech
*Attorney, Agent, or Firm*—McDonnell Boehnen Hulbert & Berghoff

[57] ABSTRACT

The present invention relates to a mammalian adrenocorticotropic hormone receptor. The invention is directed toward the isolation, characterization and pharmacological use of mammalian adrenocorticotropic hormone receptor, the gene corresponding to this receptor, a recombinant eukaryotic expression construct capable of expressing a mammalian adrenocorticotropic hormone receptor in cultures of transformed eukaryotic cells and such cultures of transformed eukaryotic cells that synthesize mammalian adrenocorticotropic hormone receptor. The invention also provides methods for screening ACTH$^R$ agonists and antagonists in vitro using preparations of receptor from such cultures of eukaryotic cells transformed with a recombinant eukaryotic expression construct comprising the ACTH$^R$ receptor gene. The invention specifically provides human and bovine ACTH$^R$ genes.

10 Claims, 10 Drawing Sheets
(2 of 10 Drawing(s) in Color)

```
  10         20         30         40         50         60         70
ACAACACTTT ATATATATTT TTATAAATGT AAGGGGTACA AARGTGCCAT TTTGTTACAT GGATATACCG
  80         90        100        110        120        130        140
TGTAGTGGTG AAGCCTGGGC TTTTAGTGTA TCTGTCATCA GAATAACATA CGTGTTACCC ATAGGAATTT
 150        160        170        180        190        200        210
CTCATCACCC GCCCCCTCCA CCCTTCGAGT CTCCAATGTC CATTCCACAC TCTATATCCA CGTGTATGCA
 220        230        240        250        260        270        280
TATAGCTCCA CATATAAGTG AGAACATGTA GTATTTGACT TCCTCTTTCT GAGTTATTTC ACTTTGATAA
 290        300        310        320        330        340        350
TGGCCTCCAC TTCCATCCAT GTTGCTGCAA AAGACATGAC CTTATTCTTT TTGATAGCTG GGGAGTACTC
 360        370        380        390        400        410        420
CATTGTGTAT ATGTACCACA TTTNCTTTTAT CCATTCACCC ATTGANGAAC ACTTAGTTGA TTCCATATCT
 430        440        450        460        470        480        490
TTGCTATTGT CACTAGTGCT GCAATAAACA TACATGTGCA GGCTCCTTCT AATATACTGA TTTATATTTT
 500        510        520        530        540        550        560
ATGGAGAGAG ATAGAGTTCT TAGCGAGTGT GCTGTTTATT TCTAGTGTAC TTGCAACTAA TATTCTGTAT
 570        580        590        600        610        620        630
ACTCCCTTTA GGTGATTGGA GATTTAACTT AGATCTCCAG CAAGTGCTAC AAGAAGAAAA GATCCTGAAG
 640        650        660        670        680        690        700
AATCAATCAA GTTTCCGTGA AGTCAAGTCC AAGTAACATC CCCGCCTTAA CCACAAGCAG GAGAAATGAA
 710        720        730        740        750        760        770
GCACATTATC AACTCGGTAT AAAACATCAA CAACACAGCA AGAAATAATT CCGACTGTCC TCGTGTGGTT
```

Figure 1A

```
       780         790         800         810         820         830         840
TTGCCGGAGG AGATATTTTT CACAATTTCC ATTGTTGGAG TTTGGAGAA TCTGATCGTC CTGCTGGCTG
       850         860         870         880         890         900         910
TGTTCAAGAA TAAGAATCTC CAGGCACCCA TGTACTTTTT CATCTGTAGC TTGGCCATAT CTGATATGCT
       920         930         940         950         960         970         980
GGGCAGCCTA TATAAGATCT TGGAAAATAT CCTGATCATA TTGAGAAACA TGGGCTATCT CAAGCCACGT
       990        1000        1010        1020        1030        1040        1050
GGCAGTTTTG AAACCACAGC CGATGACATC ATCGACTCCC TGTTTGTCCT CTCCCTGCTT GGCTCCATCT
      1060        1070        1080        1090        1100        1110        1120
TCAGCCTGTC TGTGATTGCT GCGGACCGCT ACATCACCAT CTTCCACGCA CTGCGGTACC ACAGCATCGT
      1130        1140        1150        1160        1170        1180        1190
GACCATGCGC CGCACTGTGG TGGTGCTTAC GGTCATCTGG ACGTTCTGCA CGGGGACTGG CATCACCATG
      1200        1210        1220        1230        1240        1250        1260
GTGATCTTCT CCCATCATGT GCCCACAGTG ATCACCTTCA CGTCGGCTGT CCCGCTGATG CTGGTCTTCA
      1270        1280        1290        1300        1310        1320        1330
TCCTGTGCCT CTATGTGCAC ATGTTCCTGC TGGCTCGATC CCACACCAGG AAGATCTCCA CCCTCCCCAG
      1340        1350        1360        1370        1380        1390        1400
AGCCAACATG AAAGGGGCCA TCACACTGAC CATCCTGCTC GGGGTCTTCA TCTTCTGCTG GGCCCCTTT
      1410        1420        1430        1440        1450        1460        1470
GTGCTTCATG TCCTCTTGAT GACATTCTGC CCAAGTAACC CCTACTGCGC CTGCTACATG TCTCTCTTCC
```

Figure 1B

```
1480                 1490       1500       1510       1520       1530       1540
AGGTGAACGG    CATGTTGATC ATGTGCAATG CCGTCATTGA CCCCTTCATA TATGCCTTCC GGAGCCCAGA
    1550       1560       1570       1580       1590       1600       1610
GCTCAGGGAC GCATTCAAAA AGATGATCTT CTGCAGCAGG TACTGGTAGA ATGGCTGATC CCTGGTTTTA
    1620       1630       1640       1650       1660       1670       1680
GAATCCATGG GAATAACGTT GCCAAGTGCC AGAATAGTGT AACATTCCAA CAAATGCCAG TGCTCCTCAC
    1690       1700       1710       1720       1730       1740       1750
TGGCCTTCCT TCCCTAATGG ATGCAAGGAT GACCCACCAG CTAGTGTTTC TGAATACTAT GGCCAGGAAC
    1760       1770       1780       1790       1800       1810       1820
AGTCTATTGT AGGGGCAACT CTATTTGTGA CTGGACAGAT AAAACGTGTA GTAAAAGAAG GATAGAATAC
    1830       1840       1850       1860       1870       1880       1890
AAAGTATTAG GTACAAAAGT AATTANGGTT TNNGCNATTA CTTNNMATGA CNNNAAATNG CANTTACTTT
    1900       1910       1920       1930       1940       1950       1960
TGCACCAATC TAGTAAAACA GCAATAAAAA TTCAAGGGCT TTGGGCTAAG GCAAAGACTT GCTTTCCTGT
    1970       1980       1990       2000       2010       2020
GGACATSTAA CAAGCCAGTT CTGANGGCGG CCTTTCCAGG TGGAGGCCAT TGCAGCCAAT TTCAGAGT
```

Figure 1C

```
         10         20         30         40         50         60         70
GGGGCCAGAA AGTTCCTGCT TCAGAGCAGA AGATCTTCAG CAAGAACTAC AAAGAAGAAA AGATTCTGGA
         80         90        100        110        120        130        140
GAATCAATCA AGTTTCCTGT CAAGTTCCAG TAACGTTTCT GTCTTAACTG CACACAGGAA AGATGAAACA
        150        160        170        180        190        200        210
CATTCTCAAT CTGTATGAAA ACATCAACAG TACAGCAAGA AATAACTCAG ACTGTCCTGC TGTGATTTTG
        220        230        240        250        260        270        280
CCAGAAGAGA TATTTTTCAC AGTATCCATT GTTGGGGTTT TGGAGAACCT GATGGTCCTT CTGGCTGTGG
        290        300        310        320        330        340        350
CCAAGAATAA GAGTCTTCAG TCGCCCATGT ACTTTTTCAT CTGCAGCTTG GCTATTTCCG ATATGCTGGG
        360        370        380        390        400        410        420
GAGCCTGTAC AAGATTTTGG AAAACGTTCT GATCATGTTC AAAAACATGG GTTACCTCGA GCCTCGAGGC
        430        440        450        460        470        480        490
AGTTTTGAAA AGCACAGCAG ATGATGTGGT GGACTCCCTG TTCATCCCTCT CCCTTCTCGG CTCCATCTGC
        500        510        520        530        540        550        560
AGCCTGTCTG TGATTGCGCT GACCGCTCAT CACAATCTTC CACGCTCTGC AGTACCACCG CATCATGACC
        570        580        590        600        610        620        630
CCGCACCGTG CCCTCGTCAT CTGAGGGTCC TCTGGGCAGG CTGCACAGGC AGTGGCATTA CCATCGTGAC
        640        650        660        670        680        690        700
CTTCTCCCAT CACGTCCCCA CAGTGATCGC CTTCACAGCG CTGTTCCCGC TGATGCTGGC CTTCATCCTG
        710        720        730        740        750        760        770
TGCCTCTACG TGCACATGTT CCTGCTGGCC CGCTCCCACA CCAGGAGGAC CCCCTCCCTT CCCAAAGCCA
```

```
      780              790              800              810              820              830              840
ACATGAGAGG       GGCCGTCACA       CTGACTGTCC       TGCTCGGGGT       CTTCATTTTC       TGTTGGGCAC       CCTTTGTCCT
      850              860              870              880              890              900              910
TCATGTCCTC       TTGATGACAT       TCTGCCCCAG       TGACCCCTAG       TGTGCCTGCT       ACATGTCCCT       CTTCCAGGTG
      920              930              940              950              960              970              980
AATGGTGTGT       TGATCATGTG       TAATGCCATC       ATCGACCCCT       TCATATATGC       CTTCGGAGCC       CAGAGCTCAG
      990             1000             1010             1020             1030             1040             1050
GGTCGCATTC       AAAAAGATGG       TTTATCTGCA       ACTGTTACCA       GTAGAATGAT       TGGTCCCTGA       TTTTAGGAGC
     1060             1070             1080             1090             1100
CACAGGGATA       TACTGTCAGG       GACAGAGTAG       CGTGACAGAC       CAACAACACT       AGGACT
```

Figure 3A

```
mouse MSH-R              mstQepQksLvGSLNSnaTsh--                                       21
human MSH-R              mavQgsQrrLlGSLNStpTaipq                                       23
human ACTH-R                                     mkhiinsye                              9
rat cannab.                                                m-(101)----------------    102

I                                        II
mouse MSH-R    LGLATNQsepwClyVSIPDGLFLSLGLVSLVENvLVViAItKNRNLHcPMYyFICCLALSD            82
human MSH-R    LGLAaNQtgarCleVSIsDGLFLSLGLVSLVENaLVvatIaKNRNLHsPMYcFICCLALSD            84
human ACTH-R   ninnTarnnsdCprVvlPeeifFTisiVgvlENliVllAvfKNkNLqaPMYfFICsLAiSD            70
rat cannab.    --------------------L-LTLG---VLENLLVL--I--R-L--P-Y-FI-SLA---D          163

III
mouse MSH-R    LmVSvsiVLETtiILLLEvGiLVARvAlvQQLDNlIDVliCgSMvSSLCFLGiIAiDRYIS           143
human MSH-R    LLVSgtnVLETavILLLEaGaLVARaAvlQQLDNvIDVitCsSMLSSLCFLGaIAvDRYIS           145
human ACTH-R   mLgSlyklLEnillilLrnmGyLkpRgsfettaDdiIDslfvlSlLgSifsLsvIaaDRYIt          131
rat cannab.    LLGSV--V------------F----------------V----GSLF-L---AIDRYIS             224
```

Figure 3B

```
                            IV                                                        V
mouse MSH-R   IFYALRYHSIVTLPRArRAVvgIWmvSivsSTLFItyYkhtAVLLCLvtFFLAMLaIMAiL  204
HUMAN MSH-R   IFYALRYHSIVTLPRApRAVaaIWvaSvVfSTLFIaYYdHVAVLLCLvvFFLAMLVLMAvL  206
human ACTH-R  IFhALRYHSIVTmrRtvvvltvIWTfctgtgitmvifshHVptvitftslFplMLVfilcL  192
rat cannab.   I---L-Y---IVT-P-AVVA----WT--IV---L---------------FPL----L---  285

VI
mouse MSH-R   YaHMFtRACQHvQGIAqLHKRQRsirQGFsLKGAaTLTILLGIFFLCWGPFFLHLLLIVLC  264
human MSH-R   YVHMLaRACQHaQGIARLHKRQRpvhQGFgLKGAvTLTILLGIFFLCWGPFFLHtLIVLC  266
human ACTH-R  ----------lIARsHtRkistlpranmKGAiTLTILLGvFifCWaPFvLHvLLmtfC  245
rat cannab.   -------(31)----RP----R----A-TL---L-V-I-CWGP------------  373
                                    VII
mouse MSH-R   PqHPTCsCIFKNFNLFLLLIvlsstvDPLIYAFRSQELRmTLKEVLlCS--W  317
human MSH-R   PeHPTCgCIFKNFNLFLFLaLIiCNAiIDPLIYAFhSQELRrTLKeVLtCS--W  316
human ACTH-R  PsnPyCaCymslFqvngMLImCNAvIDPfIYAFRSpKLRdafKkmlfCSryW  297
rat cannab.   ------I----F----ML--LNSTV-P-IYA-RS---LR-AF--M-F-S---(56)  483
```

MAMMALIAN ADRENOCORTICOTROPIC HORMONE RECEPTORS AND USES

This is a divisional of application Ser. No. 08/077,673, filed on Jun. 15, 1993, now U.S. Pat. No. 5,554,729, issued Sep. 10, 1996, which is a divisional of Ser. No. 07/866,560, filed Apr. 10, 1992, now U.S. Pat. No. 5,280,112, issued Jan. 18, 1994.

This invention was made with government support under 1R01DK41921-03, 1R01DK43859-01, and 1P01DK44239-10A1 by the National Institutes of Health. The government has certain rights in the invention.

BACKGROUND OF THE INVENTION

1. Field of the Invention

This invention relates to adrenocorticotropic hormone receptors from mammalian species and the genes corresponding to such receptors. Specifically, the invention relates to the isolation, cloning and sequencing of a human adrenocorticotropic hormone receptor gene. The invention also relates to the isolation, cloning and sequencing of a bovine adrenocorticotropic hormone receptor gene. The invention relates to the construction of eukaryotic recombinant expression constructs capable of expressing these adrenocorticotropic hormone receptors in cultures of transformed eukaryotic cells, and the production of the adrenocorticotropic hormone receptor in such cultures. The invention relates to the use of such cultures of transformed eukaryotic cells to produce homogeneous compositions of such adrenocorticotropic hormone receptors. The invention also provides culture of such cells producing adrenocorticotropic hormone receptor for the characterization of novel and useful drugs. 2. Background of the Invention The proopiomelanocortin (POMC) gene product is processed to produce a large number of biologically active peptides. Two of these peptides, alpha-melanocyte stimulating hormone (αMSH), and adrenocorticotropic hormone (ACTH) have well understood roles in control of melanocyte and adrenocortical function, respectively. Both of these hormones, however, are found in a variety of forms with unknown functions. The melanocortin peptides also have a diverse array of biological activities in other tissues, including the brain, and immune system, and bind to specific receptors there with a distinct pharmacology [see, Hanneman et al., in *Peptide Hormone as Prohormones*, G. Martinez, ed. (Ellis Horwood Ltd.: Chichester, UK) pp. 53–82; DeWied & Jolles, 1982, Physiol. Rev. 62: 976–1059 for reviews].

A complete understanding of these peptides and their diverse biological activities requires the isolation and characterization of their corresponding receptors. Some biochemical studies have been reported on the prior art.

Oelofsen & Ramachandran, 1983, Arch. Biochem. Biophys. 225: 414–421 disclose receptor binding studies on ACTH receptors on rat adipocytes.

Mertz & Catt, 1991, Proc. Natl. Acad. Sci. USA 88: 8525–8529 disclose functional expression of ACTH receptors in *Xenopus laevis* oocytes following injection of total cellular RNA from adrenal tissue.

Moore et al., 1991, Endocrinology 34: 107–114 relates to Allgrove syndrome, an autosomal recessive syndrome characterized by ACTH insensitivity.

The present invention comprises a human adrenocorticotropic hormone receptor gene, the nucleotide sequence of this gene and the deduced amino acid sequence of its cognate protein, a homogeneous composition of the adrenocorticotropic hormone receptor, nucleic acid hybridization probes and a method for determining the tissue distribution of expression of the gene, a recombinant expression construct capable of expressing the gene in cultures of transformed eukaryotic cells, and such cultures of transformed eukaryotic cells useful in the characterization of novel and useful drugs. The present invention also comprises the bovine adrenocorticotropic hormone receptor gene.

SUMMARY OF THE INVENTION

The present invention relates to the cloning, expression and functional characterization of mammalian adrenocorticotropic hormone receptor ($ACTH^R$) genes. The invention comprises the nucleotide sequence of these genes encoding the mammalian $ACTH^R$s and the deduced amino acid sequences of the cognate proteins, as well as tissue distribution patterns of expression of these genes.

In particular, the present invention is directed toward the isolation, characterization and pharmacological use of the human $ACTH^R$, the gene corresponding to this receptor, a nucleic acid hybridization probe comprising DNA sequences of the human $ACTH^R$, a recombinant eukaryotic expression construct capable of expressing the human $ACTH^R$ in cultures of transformed eukaryotic cells and such cultures of transformed eukaryotic cells that synthesize the human $ACTH^R$, a homogeneous composition of the human $ACTH^R$, and antibodies against and epitopes of the human $ACTH^R$.

The present invention is also directed toward the isolation, characterization and pharmacological use of the bovine $ACTH^R$, the gene corresponding to this receptor, a nucleic acid hybridization probe comprising DNA sequences of the bovine $ACTH^R$, a recombinant eukaryotic expression construct capable of expressing the bovine $ACTH^R$ in cultures of transformed eukaryotic cells and such cultures of transformed eukaryotic cells that synthesize the bovine $ACTH^R$, a homogeneous composition of the bovine $ACTH^R$, and antibodies against and epitopes of the bovine $ACTH^R$.

It is an object of the invention to provide a nucleotide sequence encoding a mammalian $ACTH^R$. In a preferred embodiment of the invention, the nucleotide sequence encodes the human $ACTH^R$. In another preferred embodiment, the nucleotide sequence encodes the bovine $ACTH^R$.

The present invention includes a nucleotide sequence encoding a human $ACTH^R$ receptor derived from a DNA molecule isolated from a human genomic library (SEQ ID NO:3). In this embodiment of the invention, the nucleotide sequence includes 2028 nucleotides of the human $ACTH^R$ gene comprising 893 nucleotides of coding sequence, 696 nucleotides of 5' untranslated sequence and 439 nucleotides of 3' untranslated sequence.

The present invention also includes a nucleotide sequence encoding a bovine $ACTH^R$R derived from a cDNA molecule isolated from a cDNA library constructed with bovine RNA (SEQ ID NO:5). In this embodiment of the invention, the nucleotide sequence includes 1106 nucleotides of the bovine $ACTH^R$ gene comprising 893 nucleotides of coding sequence, 133 nucleotides of 5' untranslated sequence and 82 nucleotides of 3' untranslated sequence.

The invention includes nucleotide sequences of mammalian $ACTH^R$s, most preferably bovine and human $ACTH^R$s (SEQ ID NOs:5&3), and includes allelic variations of these nucleotide sequences and the corresponding $ACTH^R$ molecule, either naturally occurring or the product of in vitro chemical or genetic modification, each such variant having essentially the same nucleotide sequence as the nucleotide sequence of the corresponding ACTH$^R$ disclosed herein, wherein the resulting ACTH$^R$ molecule has substantially the same biological properties as the ACTH$^R$ molecule corresponding to the nucleotide sequence described herein. The term "substantially homologous to" as used in this invention encompasses such allelic variability as described in this paragraph.

The invention also includes a predicted amino acid sequence for the bovine (SEQ ID NO:6) and human (SEQ ID NO:4) ACTH$^R$ deduced from the nucleotide sequence comprising the complete coding sequence of the bovine (SEQ ID NO:5) and human (SEQ ID NO:3) ACTH$^R$R gene as described herein.

In another aspect, the invention comprises a homogeneous composition of a 34 kilodalton bovine ACTH$^R$ or derivative thereof, wherein the amino acid sequence of the ACTH$^R$ or derivative thereof comprises a sequence shown in FIG. 3 (SEQ ID NO:6).

In another aspect, the invention comprises a homogeneous composition of a 34 kilodalton human ACTH$^R$ or derivative thereof, wherein the amino acid sequence of the ACTH$^R$ or derivative thereof comprises a sequence shown in FIG. 3 (SEQ ID NO:4).

This invention provides both nucleotide and amino acid probes derived from these sequences. The invention includes probes isolated from either cDNA or genomic DNA clones, as well as probes made synthetically with the sequence information derived therefrom. The invention specifically includes but is not limited to oligonucleotide, nick-translated, random primed, or in vitro amplified probes made using cDNA or genomic clone embodying the invention, and oligonucleotide and other synthetic probes synthesized chemically using the nucleotide sequence information of cDNA or genomic clone embodiments of the invention.

It is a further object of this invention to provide sequences of mammalian ACTH$^R$, preferably the bovine or human ACTH$^R$, for use as nucleic acid hybridization probes to determine the pattern, amount and extent of expression of this receptor in various tissues of mammals, including humans. It is also an object of the present invention to provide nucleic acid hybridization probes derived from the sequences of the bovine or human ACTH$^R$ to be used for the detection and diagnosis of genetic diseases. It is an object of this invention to provide nucleic acid hybridization probes derived from the DNA sequences of the bovine or human ACTH$^R$ to be used for the detection of novel related receptor genes.

The present invention also includes synthetic peptides made using the nucleotide sequence information comprising cDNA or genomic clone embodiments of the invention. The invention includes either naturally occurring or synthetic peptides which may be used as antigens for the production of ACTH$^R$-specific antibodies, or used for competitors of the ACTH$^R$ molecule for drug binding, or to be used for the production of inhibitors of the binding of agonists or antagonists or analogues thereof to ACTH$^R$ molecule.

The present invention also provides antibodies against and epitopes of mammalian ACTH$^R$s, preferably bovine or human ACTH$^R$ proteins. It is an object of the present invention to provide antibodies that is immunologically reactive to a mammalian ACTH$^R$ protein. It is a particular object of the invention to provide a monoclonal antibodies to mammalian ACTH$^R$ protein, most preferably bovine or human ACTH$^R$ protein.

It is also an object of the present invention to provide a hybridoma cell line that produces such an antibody. It is a particular object of the invention to provide a hybridoma cell line that is the result of fusion between a non-immunoglobulin producing bovine myeloma cell line and spleen cells derived from a bovine immunized with a human cell line which expresses ACTH$^R$ antigen. The present invention also provides a hybridoma cell line that produces such an antibody, and that can be injected into a living bovine to provide an ascites fluid from the bovine that is comprised of such an antibody.

The present invention also provides a pharmaceutical composition comprising a therapeutically effective amount of a monoclonal antibody that is immunologically reactive to a mammalian ACTH$^R$, preferably a bovine or human ACTH$^R$R, and in a pharmaceutically acceptable carrier.

It is a further object of the present invention to provide an epitope of a mammalian ACTH$^R$ protein wherein the epitope is immunologically reactive to an antibody specific for the mammalian ACTH$^R$. In preferred embodiments, the epitope is derived from bovine of human ACTH$^R$ protein.

It is another object of the invention to provide a chimeric antibody that is immunologically reactive to a mammalian ACTH$^R$ protein. In a preferred embodiment, the chimeric antibody is a monoclonal antibody. In a preferred embodiment, the ACTH$^R$ is a bovine or human ACTH$^R$.

The present invention provides a recombinant expression construct comprising the nucleotide sequence of a mammalian ACTH$^R$, preferably the bovine or human ACTH$^R$ and sequences sufficient to direct the synthesis of bovine or human ACTH$^R$ in cultures of transformed eukaryotic cells. In a preferred embodiment, the recombinant expression construct is comprised of plasmid sequences derived from the plasmid pcDNAI/neo and cDNA or genomic DNA of bovine or human ACTH$^R$ gene. This invention includes a recombinant expression construct comprising essentially the nucleotide sequences of genomic or cDNA clones of bovine or human ACTH$^R$ in an embodiment that provides for their expression in cultures of transformed eukaryotic cells.

It is also an object of this invention to provide cultures of transformed eukaryotic cells that have been transformed with such a recombinant expression construct and that synthesize mammalian, preferably bovine or human, ACTH$^R$ protein. In a preferred embodiment, the invention provides human 293 cells that synthesize bovine ACTH$^R$. In an additional preferred embodiment, the invention provides human 293 cells that synthesize human ACTH$^R$ protein.

The present invention also includes protein preparations of mammalian, preferably bovine or human ACTH$^R$, and preparations of membranes containing mammalian ACTH$^R$, derived from cultures of transformed eukaryotic cells. In a preferred embodiment, cell membranes containing bovine ACTH$^R$ protein are isolated from 293 cell cultures transformed with a recombinant expression construct that directs the synthesis of bovine ACTH$^R$. In another preferred embodiment, cell membranes containing human ACTH$^R$ protein are isolated from 293 cell cultures transformed with a recombinant expression construct that directs the synthesis of human ACTH$^R$.

It also an object of this invention to provide mammalian, preferably bovine or human ACTH$^R$ for use in the in vitro screening of novel adenosine agonist and antagonist compounds. In a preferred embodiment, membrane preparations containing the bovine ACTH$^R$, derived from cultures of transformed eukaryotic cells, are used to determine the drug dissociation properties of various novel adenosine agonist and antagonist compounds in vitro. In another preferred embodiment, membrane preparations containing the human ACTH$^R$, derived from cultures of transformed eukaryotic cells, are used to determine the drug dissociation properties of various novel adenosine agonist and antagonist compounds in vitro. These properties are then used to characterize such novel compounds by comparison to the binding properties of known bovine or human ACTH$^R$ agonists and antagonists.

The present invention is also useful for the in vitro detection of analogues of agonists or antagonists of ACTH$^R$, known or unknown, either naturally occurring or as the embodiments of a drug.

It is an object of the present invention to provide a method for the quantitative detection of agonists or antagonists, or analogues thereof, of ACTH$^R$, known or unknown, either naturally occurring or as the embodiments of a drug. It is an additional object of the invention to provide a method to detect such agonists, antagonists, or analogues thereof in blood, saliva, semen, cerebrospinal fluid, plasma, lymph, or any other bodily fluid.

Specific preferred embodiments of the present invention will become evident from the following more detailed description of certain preferred embodiments and the claims.

The file of this patent contains at least one drawing executed in color. Copies of this patent with color drawing (s) will be provided by the Patent and Trademark Office upon request and the payment of the necessary fee.

DESCRIPTION OF THE DRAWINGS

FIGS. 1A–1C illustrate the nucleotide sequence of the human (SEQ ID NO:3) adrenocorticotropic hormone receptor.

FIGS. 2A through 2B illustrates the nucleotide sequence of the bovine (SEQ ID NO:5) adrenocorticotropic hormone receptor.

FIGS. 3A through 3B presents an amino acid sequence comparison between the human adrenocorticotropic hormone receptor protein and the mouse and human melanocyte stimulating hormone receptor proteins.

DETAILED DESCRIPTION OF THE PREFERRED EMBODIMENTS

Figure 4:
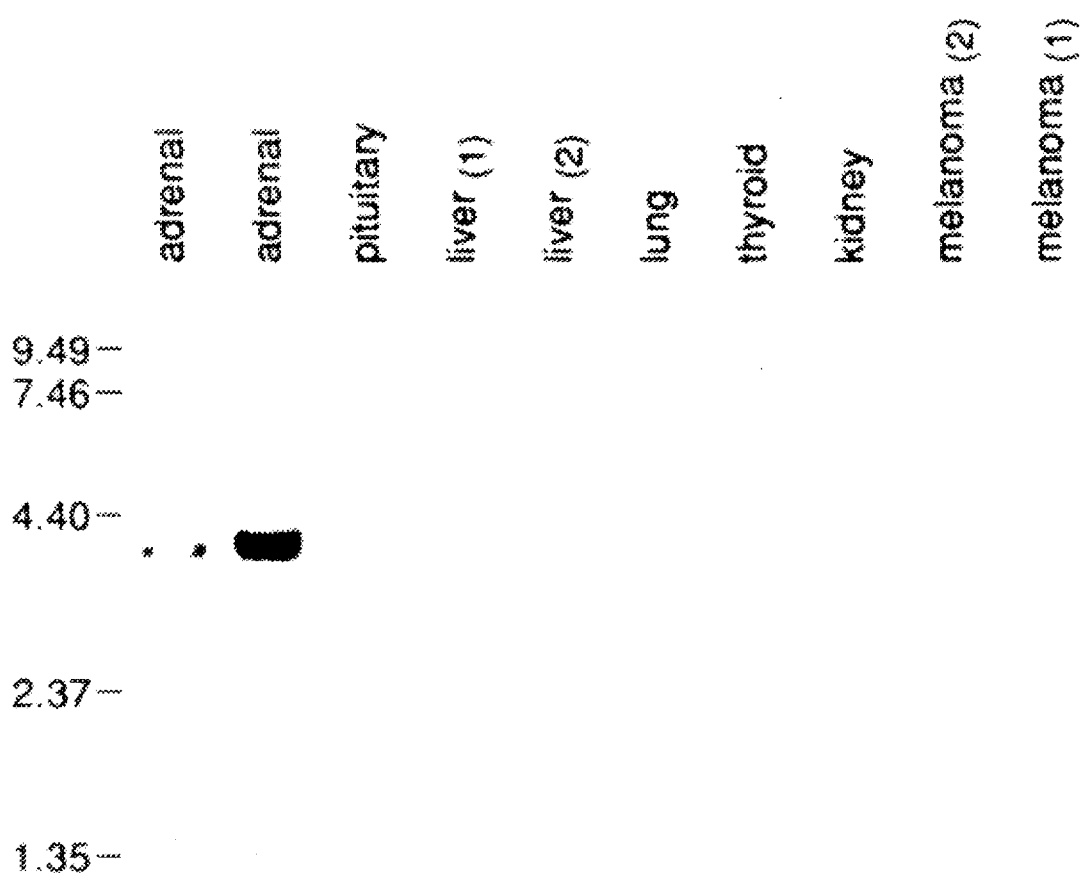
FIG. 4 illustrates the tissue distribution of human adrenocorticotropic hormone receptor gene expression by Northern blot hybridization.

The term "adrenocorticotropic hormone receptor" as used herein refers to proteins substantially homologous to, and having substantially the same biological activity as, the protein coded for by the nucleotide sequence depicted in FIGS. 1A and 1B (SEQ ID No:3) and FIGS. 2A and 2B (SEQ ID No.:5). This definition is intended to encompass natural allelic variations in the adrenocorticotropic hormone receptor sequence. Cloned genes of the present invention may code for ACTH$^R$s of any species of origin, including, for example, bovine, rat, rabbit, cat, and human, but preferably code for receptors of mammalian, most preferably bovine and human, origin.

Nucleic acid hybridization probes provided by the invention comprise DNA sequences that are substantially homologous to the DNA sequences in FIGS. 1A and 1B (SEQ ID NO:3) and FIGS. 2A and 2B (SEQ ID NO:5). Nucleic acid probes are useful for detecting ACTH$^R$ gene expression in cells and tissues using techniques well-known in the art, including but not limited to Northern blot hybridization, in situ hybridization and Southern hybridization to reverse transcriptase—polymerase chain reaction product DNAs. The probes provided by the present invention, including oligonucleotides probes derived therefrom, are useful are also useful for Southern hybridization of mammalian, preferably human, genomic DNA for screening for restriction fragment length polymorphism (RFLP) associated with certain genetic disorders.

The production of proteins such as the ACTH$^R$ from cloned genes by genetic engineering is well known. See, e.g., U.S. Pat. No. 4,761,371 to Bell et al. at Col. 6 line 3 to Col. 9 line 65. (The disclosure of all U.S. patent references cited herein is to be incorporated herein by reference.) The discussion which follows is accordingly intended as an overview of this field, and is not intended to reflect the full state of the art.

DNA which encodes the ACTH$^R$ may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the ACTH$^R$ gene sequence information provided herein. Probes may be labeled with a detectable group such as a fluorescent group, a radioactive atom or a chemiluminescent group in accordance with know procedures and used in conventional hybridization assays, as described in greater detail in the Examples below. In the alternative, ACTH$^R$ gene sequences may be obtained by use of the polymerase chain reaction (PCR) procedure, with the PCR oligonucleotide primers being produced from the ACTH$^R$R gene sequence provided herein. See U.S. Pat. Nos. 4,683,195 to Mullis et al. and 4,683,202 to Mullis.

The ACTH$^R$ may be synthesized in host cells transformed with a recombinant expression construct comprising a DNA sequence encoding the ACTH$^R$. Such a recombinant expression construct can also be comprised of a vector that is a replicable DNA construct. Vectors are used herein either to amplify DNA encoding the ACTH$^R$ and/or to express DNA which encodes the ACTH$^R$. For the purposes of this invention, a recombinant expression construct is a replicable DNA construct in which a DNA sequence encoding the ACTH$^R$ is operably linked to suitable control sequences capable of effecting the expression of the ACTH$^R$ in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. A preferred vector is the plasmid pcDNAI/neo. Transformed host cells are cells which have been transformed or transfected with recombinant expression constructs made using recombinant DNA techniques and comprising a mammalian $ACTH^R$. Transformed host cells may ordinarily express the mammalian $ACTH^R$, but host cells transformed for purposes of cloning or amplifying nucleic acid hybridization probe DNA need not express the receptor. When expressed, the mammalian $ACTH^R$ will typically be located in the host cell membrane.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leaders sequences, contiguous and in the same translational reading frame.

Cultures of cells derived from multicellular organisms are a desirable host for recombinant $ACTH^R$ synthesis. In principal, any higher eukaryotic cell culture is workable, whether from vertebrate or invertebrate culture. However, mammalian cells are preferred, as illustrated in the Examples. Propagation of such cells in cell culture has become a routine procedure. See *Tissue Culture,* Academic Press, Kruse & Patterson, editors (1973). Examples of useful host cell lines are human 293 cells, VERO and HeLa cells, Chinese hamster ovary (CHO) cell lines, and WI138, BHK, COS-7, CV, and MDCK cell lines. Human 293 cells are preferred. Expression vectors for such cells ordinarily include (if necessary) an origin of replication, a promoter located upstream from the gene to be expressed, along with a ribosome binding site, RNA splice sites (if intron-containing genomic DNA is used), a polyadenylation site, and a transcriptional termination sequence.

An origin of replication may be provided either by construction of the vector to include an exogenous origin, such as may be derived from SV40 or other viral source (e.g., polyoma, adenovirus, VSV, or MPV), or may be provided by the host cell chromosomal replication mechanism. If the vector is integrated into the host cell chromosome, the latter may be sufficient.

The invention provides homogeneous compositions of mammalian $ACTH^R$ protein produced by transformed eukaryotic cells as provided herein. Such homogeneous compositions are intended to be comprised of mammalian $ACTH^R$ protein that comprises 90% of the protein in such homogeneous composition.

Mammalian $ACTH^R$ protein made from cloned genes in accordance with the present invention may be used for screening agonist compounds for $ACTH^R$ activity, or for determining the amount of a $ACTH^R$ agonist or antagonist drug in a solution (e.g., blood plasma or serum). For example, host cells may be transformed with a recombinant expression construct of the present invention, $ACTH^R$ expressed in that host, the cells lysed, and the membranes from those cells used to screen compounds for $ACTH^R$ binding activity. Competitive binding assays in which such procedures may be carried out are well known in the art. By selection of host cells which do not ordinarily express $ACTH^R$s, pure preparations of membranes containing $ACTH^R$s can be obtained. Further, $ACTH^R$ agonists and antagonists can be identified by transforming host cells with vectors of the present invention. Membranes obtained from such cells can be used in binding studies wherein the drug dissociation activity is monitored.

The recombinant expression constructs of the present invention are useful in molecular biology to transform cells which do not ordinarily express the $ACTH^R$ to thereafter express this receptor. Such cells are useful as intermediates for making cell membrane preparations useful for receptor binding assays, which are in turn useful for drug screening. Further, genes and vectors comprising the recombinant expression construct of the present invention are useful in gene therapy. For such purposes, retroviral vectors as described in U.S. Pat. No. 4,650,764 to Temin & Watanabe or U.S. Pat. No. 4,861,719 to Miller may be employed. Cloned genes of the present invention, or fragments thereof, may also be used in gene therapy carried out homologous recombination or site-directed mutagenesis. See general Thomas & Capecchi, 1987, Cell 51: 503–512; Bertling, 1987, Bioscience Reports 7: 107–112; Smithies et al., 1985, Nature 317: 230–234.

Oligonucleotides of the present invention are useful as diagnostic tools for probing ACTH-receptor gene expression in tissues. For example, tissues can be probed in situ with oligonucleotide probes carrying detectable groups by conventional autoradiography techniques, as explained in greater detail in the Examples below, to investigate native expression of this receptor or pathological conditions relating thereto. Further, chromosomes can be probed to investigate the presence or absence of the $ACTH^R$ gene, and potential pathological conditions related thereto, as also illustrated by the Examples below.

The invention also provides antibodies that are immunologically reactive to a mammalian $ACTH^R$. The antibodies provided by the invention can be raised in animals by inoculation with cells that express a mammalian $ACTH^RR$ or epitopes of a mammalian $ACTH^R$ using methods well known in the art. Animals that can be used for such inoculations include individuals from species comprising cows, sheep, pigs, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell line which naturally expresses a mammalian $ACTH^R$, or any cell or cell line that expresses a mammalian $ACTH^R$ or any epitope therein as a result of molecular or genetic engineering, or that has been treated to increase the expression of a mammalian $ACTH^R$ by physical, biochemical or genetic means. Preferred cells are human cells, most preferably human 293 cells that have been transformed with a recombinant expression construct comprising DNA sequences encoding a mammalian $ACTH^R$ and that express the mammalian $ACTH^R$ gene product.

The present invention provides monoclonal antibodies that are immunologically reactive with an epitope that is a mammalian $ACTH^R$ present on the surface of mammalian cells, preferably human or bovine cells. These antibodies are made using methods and techniques well known to those of skill in the art.

Monoclonal antibodies provided by the present invention are produced by hybridoma cell lines, that are also provided by the invention and that are made by methods well known in the art. Hybridoma cell lines are made by fusing individual cells of a myeloma cell line with spleen cells derived from animals immunized with cells expressing a mammalian ACTH^R, including human cells, as described above. The myeloma cell lines used in the invention include lines derived from myelomas of mice, rats, hamsters, primates and humans. Preferred myeloma cell lines are from bovine, and the most preferred bovine myeloma cell line is P3X63-Ag8.653. The animals from whom spleens are obtained after immunization are rats, mice and hamsters, preferably mice, most preferably Balb/c mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a bovine, and the monoclonal antibodies obtained from blood and/or ascites fluid.

Monoclonal antibodies provided by the present invention can also be produced by recombinant genetic methods well known to those of skill in the art, and the present invention encompasses antibodies made by such methods that are immunologically reactive with an epitope of a mammalian ACTH^R.

The present invention encompasses fragments of the antibody that are immunologically reactive with an epitope of a mammalian ACTH^R. Such fragments can be produced by any number of methods, including but not limited to proteolytic cleavage, chemical synthesis or preparation of such fragments by means of genetic engineering technology. The present invention also encompasses single-chain antibodies that are immunologically reactive with an epitope of a mammalian ACTH^R made by methods known to those of skill in the art.

The present invention also encompasses an epitope of a mammalian ACTH^R that is comprised of sequences and/or a conformation of sequences present in the mammalian ACTH^R molecule. This epitope may be naturally occurring, or may be the result of proteolytic cleavage of the mammalian ACTH^R molecule and isolation of an epitope-containing peptide or may be obtained by synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies, comprised of immunologically reactive light chain and heavy chain peptides to an epitope that is a mammalian ACTH^R. The chimeric antibodies embodied in the present invention include those that are derived from naturally occurring antibodies as well as chimeric antibodies made by means of genetic engineering technology well known to those of skill in the art.

The Examples which follow are illustrative of specific embodiments of the invention, and various uses thereof. They are set forth for explanatory purposes only, and are not to be taken as limiting the invention.

EXAMPLE 1

Isolation of an ACTH Receptor Probe by Random PCR Amplification of Human Melanoma cDNA Using Degenerate Oligonucleotide Primers In order to clone novel G-protein coupled receptors, human melanoma cDNA was used as template for a polymerase chain reaction (PCR)-based random cloning experiment. PCR was performed using a pair of degenerate oligonucleotide primers corresponding to the putative third and sixth transmembrane regions of G-protein coupled receptors (Libert et al., 1989, Science 244: 569–72; Zhou et al., 1990, Nature 347: 76–80). The PCR products obtained in this experiment were characterized by nucleotide sequencing. Two novel sequences representing novel G-protein-coupled receptors were identified.

PCR amplification was performed as follows. Total RNA was isolated from a human melanoma tumor sample by the guanidinium thiocyanate method (Chirgwin et al., 1979, Biochemistry 18: 5294–5299). Double-stranded cDNA was synthesized from total RNA with murine reverse transcriptase (BRL, Gaithersburg, Md.) by oligo-dT priming [Maniatis et al., *Molecular Cloning: A Laboratory Manual*, (Cold Spring Harbor Laboratory Press, Cold Spring Harbor, N.Y.), 1990]. The melanoma cDNA mixture was then subjected to 45 cycles of PCR amplification using 500 picomoles of degenerate oligonucleotide primers having the following sequence:

Primer III (sense):
GAGTCGACCTGTG(C/T)G(C/T)(C/G)AT(C/T)(A/G)CIIT(G/T)GAC(C/A)G(C/G)TAC (SEQ ID NO:1)

and

Primer VI (antisense):
CAGAATTCAG(T/A)AGGGCAICCAGCAGAI(G/C)(G/A)(T/C)GAA (SEQ ID NO:2)

in 100 μl of a solution containing 50 mM Tris-HCl (pH 8.3), 2.5 mM MgCl$_2$, 0.01% gelatin, 200 μM each dNTP, and 2.5 units of Taq polymerase (Saiki et al., 1988, Science 239: 487–491). These primers were commercially synthesized by Research Genetics Inc. (Huntsville, Ala.). Each PCR amplification cycle consisted of incubations at 94° C. for 1 min (denaturation), 45° C. for 2 min (annealing), and 72° C. for 2 min (extension).

Amplified products of the PCR reaction were extracted with phenol/chloroform and precipitated with ethanol. After digestion with EcoRI and SalI, the PCR products were separated on a 1.2% agarose gel. A slice of this gel, corresponding to PCR products of 300 basepairs (bp) in size, was cut out and purified using glass beads and sodium iodide, and then the insert was cloned into a pBKS cloning vector (Stratagene, LaJolla, Calif.).

A total of 172 of such pBKS clones containing inserts were sequenced using Sequenase (U.S. Biochemical Corp., Cleveland, Ohio) by the dideoxynucleotide chain termination method (Sanger et al., 1977, Proc. Natl. Acad. Sci. USA 74: 5463–5467). Two types of sequences homologous to other G-protein coupled receptors were identified.

EXAMPLE 2

Isolation and Characterization of Human ACTH^R Genomic Clones

In order to isolate the human gene corresponding to one of the two G-protein coupled receptor probes of Example 1, a human genomic library was screened at high stringency (50% formamide, 1M NaCl, 50 nM Tris-HCl, pH 7.5, 0.1% sodium pyrophosphate, 0.2% sodium dodecyl sulfate, 100 μg/ml salmon sperm DNA, 10X Denhardt's solution, 42° C.), using the human PCR fragments isolated as described in Example 1. Two different types of sequences were isolated, corresponding to the two PCR fragments, and were found to encode highly related G protein coupled receptors. These genomic clones were sequenced as described in Example 1. The nucleotide sequence of this clone is shown in FIGS. 1A through 1C (SEQ ID NO:3). Nucleotide sequence analysis and homology comparisons were done on the OHSU computer system with software provided by Intelligenetics Inc. (Mountain View, Calif.).

One of these genomic clones was determined to encode an human MSH receptor (see copending U.S. patent application Ser. No. 07/866,979 now U.S. Pat. No. 5,532,347). The human MSH receptor has a predicted amino acid sequence that is 75% identical and colinear with a mouse αMSH receptor cDNA sequence.

The second human genomic clone isolated encodes a highly related G-coupled receptor protein (SEQ ID NO:3). The predicted amino acid sequence (SEQ ID NO:4) of this clone (FIGS. 3A through 3B, represented as human ACTH-R) is 39% identical and also colinear, excluding the third intracellular loop and carboxy-terminal tail, with the human MSH receptor gene product (FIGS. 3A through 3B, represented as human MSH-R). The predicted molecular weight of this putative $ACTH^R$ is 33.9 kilodaltons (kD). Based on its high degree of homology to the murine (mouse MSH-R; FIGS. 3A through 3B) and human MSH receptors, and the pattern of expression in different tissue types, as described in Example 3 below, this gene is a believed to encode a human ACTH receptor.

A bovine genomic DNA clone was isolated from a bovine genomic library, essentially as described above, and its nucleotide sequence determined (FIGS. 2A through 2B; SEQ ID NO:5).

The predicted amino acid sequences of the mouse $αMSH^R$, human $MSH^R$, and the putative human $ACTH^R$ are aligned in FIGS. 3A through 3B. These sequences define the melanocortin receptors as a novel subfamily of the G protein-coupled receptors with a number of unusual features. The melanocortin receptors are the smallest G protein-coupled receptors identified to date (297-317aa) resulting from a short amino terminal extracellular domain, a short carboxy-terminal intracellular domain, and a very small third intracellular loop. The melanocortin receptors are lack several amino acid residues present in most G protein coupled receptors (see Probst et al., 1992, DNA & Cell Biol. 11: 1–20), including the proline residues in the 4th and 5th transmembrane domains, likely to introduce a bend in the alpha helical structure of the transmembrane domains and thought to be involved in the formation of the binding pocket (see Applebury & Hargrave, 1986, Vision Res. 26: 1881–1895), and one or both of the cysteine residues thought to form a disulfide bond between the first and second extracellular loops (see Dixon et al., 1987, EMBO J. 6: 3269–3275 and Karnik et al., 1988, Proc. Natl. Acad. Sci. USA 85: 8459–8463). Remarkably, the melanocortin receptors do not appear highly related to the other G protein-coupled receptors which recognize peptide ligands, such as the receptors for bombesin (see Spindel et al., 1990, Mol. Endocrinol. 4: 1956–1963) or substance K (see Masu et al., 1987, Nature 329: 836–838), but rather, are more closely related to the receptor for $\Delta^9$-tetradhydrocannabinol (see Matsuda et al., 1990, Nature 346: 561–564). For example, the human $ACTH^R$ and rat cannabinoid receptors are about 30% identical in predicted transmembrane and intracellular loop amino acid sequences. The cannabinoid receptor also lacks the conserved proline in transmembrane 5 and the cysteine in the first extracellular loop necessary for disulfide bond formation. Least parsimony analysis with the receptor sequences shown in FIG. 3 suggests the cannabinoid and melanocortin receptors may be evolutionarily related and form a subfamily distinct from the peptide receptors and the amine receptors. Regardless of whether the similarities are the result of evolutionary conservation or convergence, the sequence and putative structural similarities between the melanocortin and cannabinoid receptors may be informative in the search for the endogenous cannabinoid-like ligand.

EXAMPLE 3

Tissue Distribution of ACTH Receptor Gene Expression

To further gain insight into this receptor, we have examined the tissue distribution of its corresponding mRNA from various tissues by performing Northern hybridization experiments on RNA isolated from various tissues (see Maniatis et al., ibid.). The results of these experiments are shown in FIG. 4.

A panel of tissue samples was examined by Northern hybridization analysis performed under high stringency conditions. The nitrocellulose filter was hybridized with a putative human ACTH receptor probe to determine the distribution of receptor mRNA. In two primary human melanocyte cultures examined, the $ACTH^R$ is encoded by two mRNA species of approximately equal stoichiometry, one at 3.0 kb, and one which co-migrates with murine $αMSH^R$ mRNA at 3.9 kb.

Figure 5:
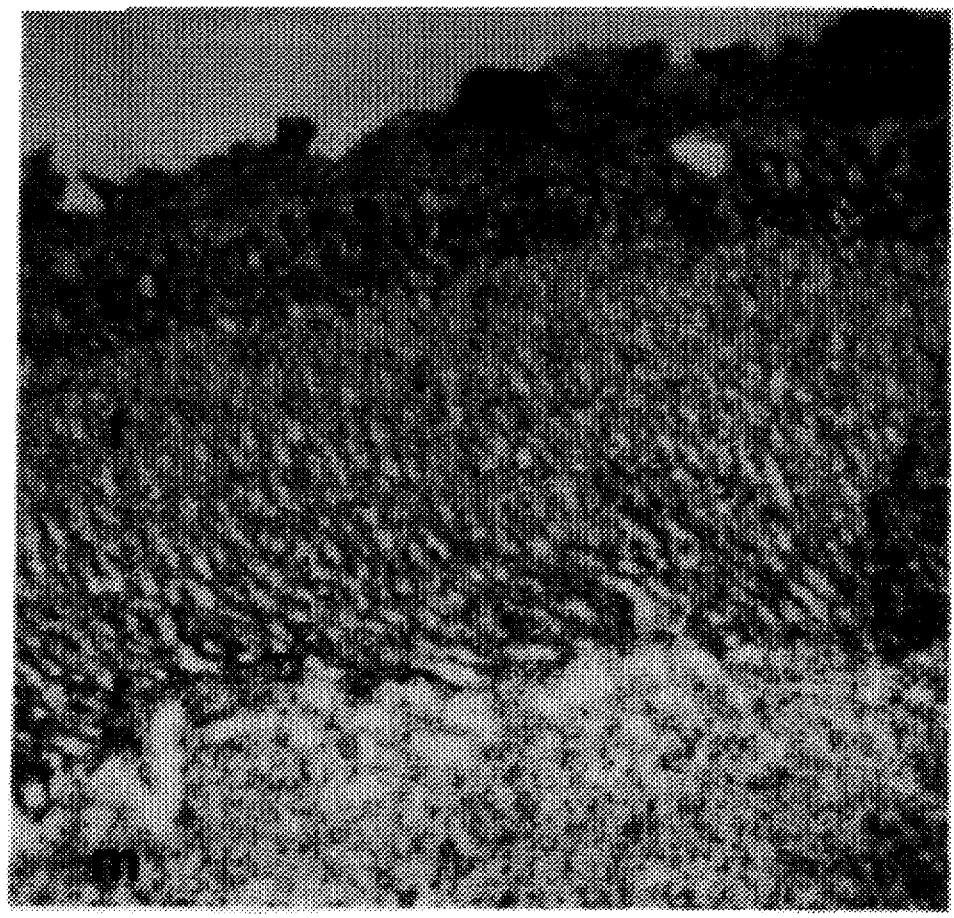
FIG. 5 illustrates localization of the putative ACTH receptor mRNA to the adrenal cortex by in situ hybridization (brightfield illumination).
Figure 6:
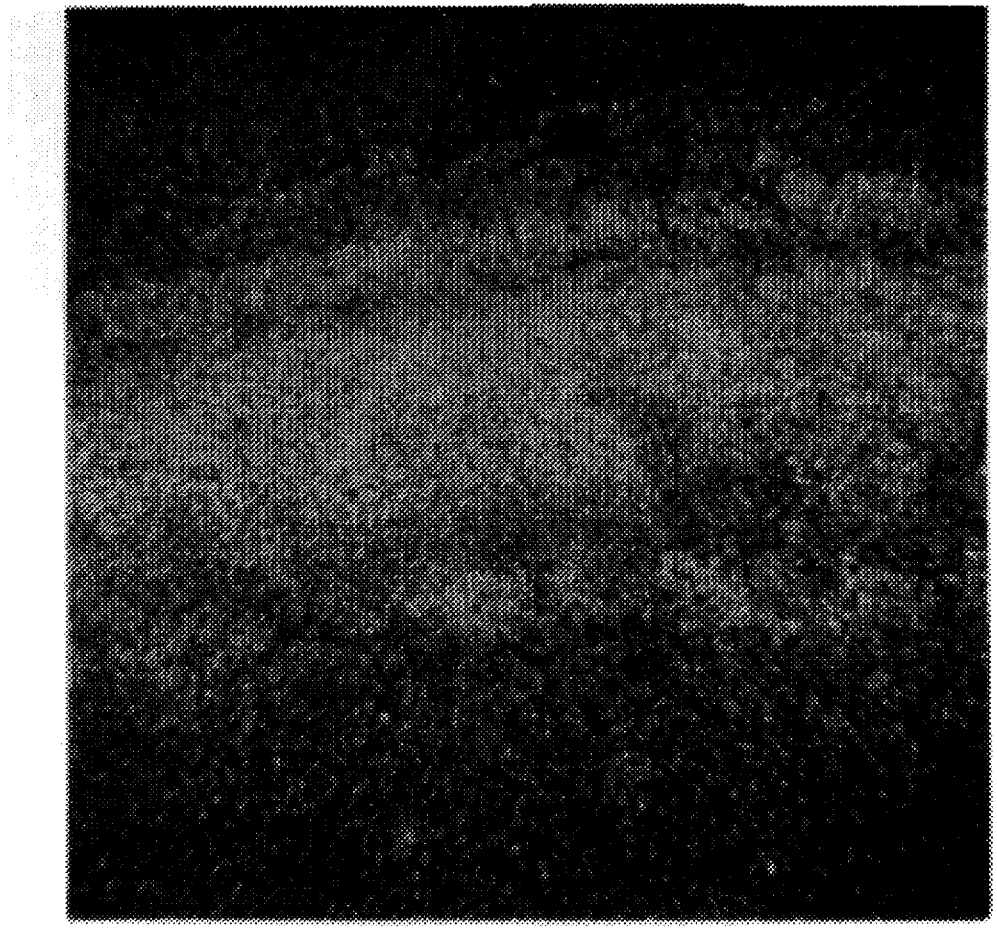
FIG. 6 illustrates localization of the putative ACTH receptor mRNA to the adrenal cortex by in situ hybridization (darkfield illumination).

The putative human ACTH receptor is encoded predominantly by a single mRNA species of approximately 4.0 kb in the human adrenal gland, although several minor species are present as well. Northern analysis of a panel of tissues from the rhesus macaque performed under high stringency conditions demonstrated the existence of a cross-reacting 4.0 kb species specific to the rhesus adrenal gland (FIG. 4). In situ hybridization of a fragment of the putative human ACTH receptor to sections of rhesus adrenal tissue localized the expression of this receptor solely to the cortex, with no apparent hybridization to the medulla or capsule, as would be predicted for this receptor (FIGS. 5 & 6). Adrenal tissue from a juvenile rhesus macaque was fixed for 24 hours in 10% formalin in phosphate buffered saline, then incubated for 24 hours in 20% sucrose in PBS. Sections were prepared and hybridized with a 600 nucleotide $^{35}$S-labelled RNA antisense probe complementary to coding sequence spanning transmembrane domains 1–6 of the putative human ACTH receptor. Hybridizations were performed at 65° C. in 2xSSC and washed at 65° C. with 0.1xSSC.

The results of these experiments are shown in FIGS. 5 & 6. FIG. 5 illustrates lightfield micrograph of an hematoxylin and eosin stained section of rhesus adrenal showing capsule (C), zona glomerulosa (G), zona fasciculata (F), zona reticulata (R), and medulla (M). FIG. 6 depicts darkfield micrograph of the same field. Within the cortex, receptor expression was found across the entire zona fasciculata, the site of glucocorticoid production, and in the cortical half of the zona glomerulosa, the site of aldosterone synthesis. The zona reticulata was largely negative, except for a small band of hybridization adjacent to the medulla, which might result from a cross-reaction between the putative ACTH$^R$ probe and a receptor for $\gamma_3$MSH, which is known to bind to this region of the adrenal cortex.

Additionally, we have been unable to detect expression in the brain of ACTH receptor described here, despite extensive documentation of ACTH binding sites there as well as in other tissues. These finding suggest the existence of alternate forms of these or related receptors that may be specifically expressed in brain tissue.

It should be understood that the foregoing disclosure emphasizes certain specific embodiments of the invention and that all modifications or alternatives equivalent thereto are within the spirit and scope of the invention as set forth in the appended claims.

---

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..33
        ( D ) OTHER INFORMATION: /function="Degenerate oligonucleotide primer (sense)"

( x i ) SEQUENCE DESCRIPTION: SEQ ID NO:1:

GAGTCGACCT GTGYGYSATY RCTKGACMGS TAC        33

( 2 ) INFORMATION FOR SEQ ID NO:2:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( i x ) FEATURE:
        ( A ) NAME/KEY: misc_feature
        ( B ) LOCATION: 1..31
        ( D ) OTHER INFORMATION: /function="Degenerate oligonucleotide primer (antisense)"

( x i ) SEQUENCE DESCRIPTION: SEQ ID NO:2:

CAGAATTCAG WAGGGCACCA GCAGASRYGA A        31

( 2 ) INFORMATION FOR SEQ ID NO:3:

( i ) SEQUENCE CHARACTERISTICS:
        ( A ) LENGTH: 2012 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 694..1587
        ( D ) OTHER INFORMATION: /product="Human adrenocorticotropic hormone receptor"

( i x ) FEATURE:

(A) NAME/KEY: 5'UTR
(B) LOCATION: 1..693

(ix) FEATURE:
(A) NAME/KEY: 3'UTR
(B) LOCATION: 1588..2012

(xi) SEQUENCE DESCRIPTION: SEQ ID NO:3:

```
ACAACACTTT ATATATATTT TTATAAATGT AAGGGGTACA AAGGTGCCAT TTTGTTACAT      60
GGATATACCG TGTAGTGGTG AAGCCTGGGC TTTTAGTGTA TCTGTCATCA GAATAACATA     120
CGTGTTACCC ATAGGAATTT CTCATCACCC GCCCCCTCCA CCCTTCGAGT CTCCAATGTC     180
CATTCCACAC TCTATATCCA CGTGTATGCA TATAGCTCCA CATATAAGTG AGAACATGTA     240
GTATTTGACT TCCTCTTTCT GAGTTATTTC ACTTTGATAA TGGCCTCCAC TTCCATCCAT     300
GTTGCTGCAA AAGACATGAC CTTATTCTTT TTGATAGCTG GGGAGTACTC CATTGTGTAT     360
ATGTACCACA TTTCTTTATC CATTCACCCA TTGAGAACAC TTAGTTGATT CCATATCTTT     420
GCTATTGTCA CTAGTGCTGC AATAAACATA CATGTGCAGG CTCCTTCTAA TATACTGATT     480
TATATTTTAT GGAGAGAGAT AGAGTTCTTA GCGAGTGTGC TGTTTATTTC TAGTGTACTT     540
GCAACTAATA TTCTGTATAC TCCCTTTAGG TGATTGGAGA TTTAACTTAG ATCTCCAGCA     600
AGTGCTACAA GAAGAAAAGA TCCTGAAGAA TCAATCAAGT TTCCGTGAAG TCAAGTCCAA     660
GTAACATCCC CGCCTTAACC ACAAGCAGGA GAA ATG AAG CAC ATT ATC AAC TCG     714
                                     Met Lys His Ile Ile Asn Ser
                                      1               5
```

| | | | | | | | | | | | | | | | | |
|---|---|---|---|---|---|---|---|---|---|---|---|---|---|---|---|---|
| TAT | GAA | AAC | ATC | AAC | AAC | ACA | GCA | AGA | AAT | AAT | TCC | GAC | TGT | CCT | CGT | 762 |
| Tyr | Glu | Asn | Ile | Asn | Asn | Thr | Ala | Arg | Asn | Asn | Ser | Asp | Cys | Pro | Arg | |
| | | 10 | | | | | 15 | | | | | 20 | | | | |
| GTG | GTT | TTG | CCG | GAG | GAG | ATA | TTT | TTC | ACA | ATT | TCC | ATT | GTT | GGA | GTT | 810 |
| Val | Val | Leu | Pro | Glu | Glu | Ile | Phe | Phe | Thr | Ile | Ser | Ile | Val | Gly | Val | |
| | 25 | | | | | 30 | | | | | 35 | | | | | |
| TTG | GAG | AAT | CTG | ATC | GTC | CTG | CTG | GCT | GTG | TTC | AAG | AAT | AAG | AAT | CTC | 858 |
| Leu | Glu | Asn | Leu | Ile | Val | Leu | Leu | Ala | Val | Phe | Lys | Asn | Lys | Asn | Leu | |
| 40 | | | | | 45 | | | | | 50 | | | | | 55 | |
| CAG | GCA | CCC | ATG | TAC | TTT | TTC | ATC | TGT | AGC | TTG | GCC | ATA | TCT | GAT | ATG | 906 |
| Gln | Ala | Pro | Met | Tyr | Phe | Phe | Ile | Cys | Ser | Leu | Ala | Ile | Ser | Asp | Met | |
| | | | | 60 | | | | | 65 | | | | | 70 | | |
| CTG | GGC | AGC | CTA | TAT | AAG | ATC | TTG | GAA | AAT | ATC | CTG | ATC | ATA | TTG | AGA | 954 |
| Leu | Gly | Ser | Leu | Tyr | Lys | Ile | Leu | Glu | Asn | Ile | Leu | Ile | Ile | Leu | Arg | |
| | | | 75 | | | | | 80 | | | | | 85 | | | |
| AAC | ATG | GGC | TAT | CTC | AAG | CCA | CGT | GGC | AGT | TTT | GAA | ACC | ACA | GCC | GAT | 1002 |
| Asn | Met | Gly | Tyr | Leu | Lys | Pro | Arg | Gly | Ser | Phe | Glu | Thr | Thr | Ala | Asp | |
| | | 90 | | | | | 95 | | | | | 100 | | | | |
| GAC | ATC | ATC | GAC | TCC | CTG | TTT | GTC | CTC | TCC | CTG | CTT | GGC | TCC | ATC | TTC | 1050 |
| Asp | Ile | Ile | Asp | Ser | Leu | Phe | Val | Leu | Ser | Leu | Leu | Gly | Ser | Ile | Phe | |
| | 105 | | | | | 110 | | | | | 115 | | | | | |
| AGC | CTG | TCT | GTG | ATT | GCT | GCG | GAC | CGC | TAC | ATC | ACC | ATC | TTC | CAC | GCA | 1098 |
| Ser | Leu | Ser | Val | Ile | Ala | Ala | Asp | Arg | Tyr | Ile | Thr | Ile | Phe | His | Ala | |
| 120 | | | | | 125 | | | | | 130 | | | | | 135 | |
| CTG | CGG | TAC | CAC | AGC | ATC | GTG | ACC | ATG | CGC | CGC | ACT | GTG | GTG | GTG | CTT | 1146 |
| Leu | Arg | Tyr | His | Ser | Ile | Val | Thr | Met | Arg | Arg | Thr | Val | Val | Val | Leu | |
| | | | | 140 | | | | | 145 | | | | | 150 | | |
| ACG | GTC | ATC | TGG | ACG | TTC | TGC | ACG | GGG | ACT | GGC | ATC | ACC | ATG | GTG | ATC | 1194 |
| Thr | Val | Ile | Trp | Thr | Phe | Cys | Thr | Gly | Thr | Gly | Ile | Thr | Met | Val | Ile | |
| | | | 155 | | | | | 160 | | | | | 165 | | | |
| TTC | TCC | CAT | CAT | GTG | CCC | ACA | GTG | ATC | ACC | TTC | ACG | TCG | CTG | TTC | CCG | 1242 |
| Phe | Ser | His | His | Val | Pro | Thr | Val | Ile | Thr | Phe | Thr | Ser | Leu | Phe | Pro | |
| | | 170 | | | | | 175 | | | | | 180 | | | | |
| CTG | ATG | CTG | GTC | TTC | ATC | CTG | TGC | CTC | TAT | GTG | CAC | ATG | TTC | CTG | CTG | 1290 |

```
Leu Met Leu Val Phe Ile Leu Cys Leu Tyr Val His Met Phe Leu Leu
    185             190                 195

GCT CGA TCC CAC ACC AGG AAG ATC TCC ACC CTC CCC AGA GCC AAC ATG        1338
Ala Arg Ser His Thr Arg Lys Ile Ser Thr Leu Pro Arg Ala Asn Met
200             205             210             215

AAA GGG GCC ATC ACA CTG ACC ATC CTG CTC GGG GTC TTC ATC TTC TGC        1386
Lys Gly Ala Ile Thr Leu Thr Ile Leu Leu Gly Val Phe Ile Phe Cys
            220             225             230

TGG GCC CCC TTT GTG CTT CAT GTC CTC TTG ATG ACA TTC TGC CCA AGT        1434
Trp Ala Pro Phe Val Leu His Val Leu Leu Met Thr Phe Cys Pro Ser
        235             240             245

AAC CCC TAC TGC GCC TGC TAC ATG TCT CTC TTC CAG GTG AAC GGC ATG        1482
Asn Pro Tyr Cys Ala Cys Tyr Met Ser Leu Phe Gln Val Asn Gly Met
    250             255             260

TTG ATC ATG TGC AAT GCC GTC ATT GAC CCC TTC ATA TAT GCC TTC CGG        1530
Leu Ile Met Cys Asn Ala Val Ile Asp Pro Phe Ile Tyr Ala Phe Arg
265             270             275

AGC CCA GAG CTC AGG GAC GCA TTC AAA AAG ATG ATC TTC TGC AGC AGG        1578
Ser Pro Glu Leu Arg Asp Ala Phe Lys Lys Met Ile Phe Cys Ser Arg
280             285             290             295

TAC TGG TAGAATGGCT GATCCCTGGT TTTAGAATCC ATGGGAATAA CGTTGCCAAG         1634
Tyr Trp

TGCCAGAATA GTGTAACATT CCAACAAATG CCAGTGCTCC TCACTGGCCT TCCTTCCCTA      1694

ATGGATGCAA GGATGACCCA CCAGCTAGTG TTTCTGAATA CTATGGCCAG GAACAGTCTA      1754

TTGTAGGGGC AACTCTATTT GTGACTGGAC AGATAAAACG TGTAGTAAAA GAAGGATAGA      1814

ATACAAAGTA TTAGGTACAA AAGTAATTAG GTTTGCATTA CTTATGACAA ATGCATTACT      1874

TTTGCACCAA TCTAGTAAAA CAGCAATAAA AATTCAAGGG CTTTGGGCTA AGGCAAAGAC      1934

TTGCTTTCCT GTGGACATTA ACAAGCCAGT TCTGAGGCGG CCTTTCCAGG TGGAGGCCAT      1994

TGCAGCCAAT TTCAGAGT                                                    2012
```

( 2 ) INFORMATION FOR SEQ ID NO:4:

( i ) SEQUENCE CHARACTERISTICS:
        ( A ) LENGTH: 297 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Lys His Ile Ile Asn Ser Tyr Glu Asn Ile Asn Asn Thr Ala Arg
1               5                   10                  15

Asn Asn Ser Asp Cys Pro Arg Val Val Leu Pro Glu Glu Ile Phe Phe
            20              25                  30

Thr Ile Ser Ile Val Gly Val Leu Glu Asn Leu Ile Val Leu Leu Ala
        35              40                  45

Val Phe Lys Asn Lys Asn Leu Gln Ala Pro Met Tyr Phe Phe Ile Cys
    50              55                  60

Ser Leu Ala Ile Ser Asp Met Leu Gly Ser Leu Tyr Lys Ile Leu Glu
65              70                  75                  80

Asn Ile Leu Ile Ile Leu Arg Asn Met Gly Tyr Leu Lys Pro Arg Gly
            85                  90                  95

Ser Phe Glu Thr Thr Ala Asp Asp Ile Ile Asp Ser Leu Phe Val Leu
            100             105                 110

Ser Leu Leu Gly Ser Ile Phe Ser Leu Ser Val Ile Ala Ala Asp Arg
            115                 120                 125
```

| | | | | | | | | | | | | | | |
|---|---|---|---|---|---|---|---|---|---|---|---|---|---|---|
|Tyr|Ile|Thr|Ile|Phe|His|Ala|Leu|Arg|Tyr|His|Ser|Ile|Val|Thr|Met|
| |130| | | |135| | | | |140| | | | |
|Arg|Arg|Thr|Val|Val|Val|Leu|Thr|Val|Ile|Trp|Thr|Phe|Cys|Thr|Gly|
|145| | | | |150| | | | |155| | | | |160|
|Thr|Gly|Ile|Thr|Met|Val|Ile|Phe|Ser|His|His|Val|Pro|Thr|Val|Ile|
| | | | |165| | | | |170| | | |175| |
|Thr|Phe|Thr|Ser|Leu|Phe|Pro|Leu|Met|Leu|Val|Phe|Ile|Leu|Cys|Leu|
| | | |180| | | | |185| | | | |190| |
|Tyr|Val|His|Met|Phe|Leu|Leu|Ala|Arg|Ser|His|Thr|Arg|Lys|Ile|Ser|
| | |195| | | | |200| | | | |205| | |
|Thr|Leu|Pro|Arg|Ala|Asn|Met|Lys|Gly|Ala|Ile|Thr|Leu|Thr|Ile|Leu|
| |210| | | | |215| | | | |220| | | |
|Leu|Gly|Val|Phe|Ile|Phe|Cys|Trp|Ala|Pro|Phe|Val|Leu|His|Val|Leu|
|225| | | | |230| | | | |235| | | | |240|
|Leu|Met|Thr|Phe|Cys|Pro|Ser|Asn|Pro|Tyr|Cys|Ala|Cys|Tyr|Met|Ser|
| | | | |245| | | | |250| | | | |255| |
|Leu|Phe|Gln|Val|Asn|Gly|Met|Leu|Ile|Met|Cys|Asn|Ala|Val|Ile|Asp|
| | | |260| | | | |265| | | | |270| | |
|Pro|Phe|Ile|Tyr|Ala|Phe|Arg|Ser|Pro|Glu|Leu|Arg|Asp|Ala|Phe|Lys|
| | |275| | | | |280| | | | |285| | | |
|Lys|Met|Ile|Phe|Cys|Ser|Arg|Tyr|Trp| | | | | | | |
| |290| | | | |295| | | | | | | | | |

( 2 ) INFORMATION FOR SEQ ID NO:5:

( i ) SEQUENCE CHARACTERISTICS:
        ( A ) LENGTH: 1108 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 133..1026

( i x ) FEATURE:
        ( A ) NAME/KEY: 5'UTR
        ( B ) LOCATION: 1..132

( i x ) FEATURE:
        ( A ) NAME/KEY: 3'UTR
        ( B ) LOCATION: 1027..1106

( x i ) SEQUENCE DESCRIPTION: SEQ ID NO:5:

```
GGGGCCAGAA AGTTCCTGCT TCAGAGCAGA AGATCTTCAG CAAGAACTAC AAAGAAGAAA        60

AGATTCTGGA GAATCAATCA AGTTTCCTGT CAAGTTCCAG TAACGTTTCT GTCTTAACTG       120

CACACAGGAA AG ATG AAA CAC ATT CTC AAT CTG TAT GAA AAC ATC AAC           168
              Met Lys His Ile Leu Asn Leu Tyr Glu Asn Ile Asn
                1               5                   10

AGT ACA GCA AGA AAT AAC TCA GAC TGT CCT GCT GTG ATT TTG CCA GAA         216
Ser Thr Ala Arg Asn Asn Ser Asp Cys Pro Ala Val Ile Leu Pro Glu
            15                  20                  25

GAG ATA TTT TTC ACA GTA TCC ATT GTT GGG GTT TTG GAG AAC CTG ATG         264
Glu Ile Phe Phe Thr Val Ser Ile Val Gly Val Leu Glu Asn Leu Met
        30                  35                  40

GTC CTT CTG GCT GTG GCC AAG AAT AAG AGT CTT CAG TCG CCC ATG TAC         312
Val Leu Leu Ala Val Ala Lys Asn Lys Ser Leu Gln Ser Pro Met Tyr
45                  50                  55                  60

TTT TTC ATC TGC AGC TTG GCT ATT TCC GAT ATG CTG GGG AGC CTG TAC         360
Phe Phe Ile Cys Ser Leu Ala Ile Ser Asp Met Leu Gly Ser Leu Tyr
```

|     |     |     |     |     | 65  |     |     |     |     | 70  |     |     |     |     | 75  |     |     |      |
|-----|-----|-----|-----|-----|-----|-----|-----|-----|-----|-----|-----|-----|-----|-----|-----|-----|-----|------|
| AAG | ATT | TTG | GAA | AAC | GTT | CTG | ATC | ATG | TTC | AAA | AAC | ATG | GGT | TAC | CTC |     |     | 408  |
| Lys | Ile | Leu | Glu | Asn | Val | Leu | Ile | Met | Phe | Lys | Asn | Met | Gly | Tyr | Leu |     |     |      |
|     |     |     |     | 80  |     |     |     |     | 85  |     |     |     |     | 90  |     |     |     |      |
| GAG | CCT | CGA | GGC | AGT | TTT | GAA | AGC | ACA | GCA | GAT | GAT | GTG | GTG | GAC | TCC |     |     | 456  |
| Glu | Pro | Arg | Gly | Ser | Phe | Glu | Ser | Thr | Ala | Asp | Asp | Val | Val | Asp | Ser |     |     |      |
|     |     | 95  |     |     |     |     | 100 |     |     |     |     | 105 |     |     |     |     |     |      |
| CTG | TTC | ATC | CTC | TCC | CTT | CTC | GGC | TCC | ATC | TGC | AGC | CTG | TCT | GTG | ATT |     |     | 504  |
| Leu | Phe | Ile | Leu | Ser | Leu | Leu | Gly | Ser | Ile | Cys | Ser | Leu | Ser | Val | Ile |     |     |      |
|     |     | 110 |     |     |     |     | 115 |     |     |     |     | 120 |     |     |     |     |     |      |
| GCC | GCT | GAC | CGC | TAC | ATC | ACA | ATC | TTC | CAC | GCT | CTG | CAG | TAC | CAC | CGC |     |     | 552  |
| Ala | Ala | Asp | Arg | Tyr | Ile | Thr | Ile | Phe | His | Ala | Leu | Gln | Tyr | His | Arg |     |     |      |
| 125 |     |     |     |     | 130 |     |     |     |     | 135 |     |     |     |     | 140 |     |     |      |
| ATC | ATG | ACC | CCC | GCA | CCG | TGC | CCT | CGT | CAT | CTG | ACG | GTC | CTC | TGG | GCA |     |     | 600  |
| Ile | Met | Thr | Pro | Ala | Pro | Cys | Pro | Arg | His | Leu | Thr | Val | Leu | Trp | Ala |     |     |      |
|     |     |     |     | 145 |     |     |     |     | 150 |     |     |     |     | 155 |     |     |     |      |
| GGC | TGC | ACA | GGC | AGT | GGC | ATT | ACC | ATC | GTG | ACC | TTC | TCC | CAT | CAC | GTC |     |     | 648  |
| Gly | Cys | Thr | Gly | Ser | Gly | Ile | Thr | Ile | Val | Thr | Phe | Ser | His | His | Val |     |     |      |
|     |     |     | 160 |     |     |     |     | 165 |     |     |     |     | 170 |     |     |     |     |      |
| CCC | ACA | GTG | ATC | GCC | TTC | ACA | GCG | CTG | TTC | CCG | CTG | ATG | CTG | GCC | TTC |     |     | 696  |
| Pro | Thr | Val | Ile | Ala | Phe | Thr | Ala | Leu | Phe | Pro | Leu | Met | Leu | Ala | Phe |     |     |      |
|     |     | 175 |     |     |     |     | 180 |     |     |     |     | 185 |     |     |     |     |     |      |
| ATC | CTG | TGC | CTC | TAC | GTG | CAC | ATG | TTC | CTG | CTG | GCC | CGC | TCC | CAC | ACC |     |     | 744  |
| Ile | Leu | Cys | Leu | Tyr | Val | His | Met | Phe | Leu | Leu | Ala | Arg | Ser | His | Thr |     |     |      |
|     | 190 |     |     |     |     | 195 |     |     |     |     | 200 |     |     |     |     |     |     |      |
| AGG | AGG | ACC | CCC | TCC | CTT | CCC | AAA | GCC | AAC | ATG | AGA | GGG | GCC | GTC | ACA |     |     | 792  |
| Arg | Arg | Thr | Pro | Ser | Leu | Pro | Lys | Ala | Asn | Met | Arg | Gly | Ala | Val | Thr |     |     |      |
| 205 |     |     |     |     | 210 |     |     |     |     | 215 |     |     |     |     | 220 |     |     |      |
| CTG | ACT | GTC | CTG | CTC | GGG | GTC | TTC | ATT | TTC | TGT | TGG | GCA | CCC | TTT | GTC |     |     | 840  |
| Leu | Thr | Val | Leu | Leu | Gly | Val | Phe | Ile | Phe | Cys | Trp | Ala | Pro | Phe | Val |     |     |      |
|     |     |     |     | 225 |     |     |     |     | 230 |     |     |     |     | 235 |     |     |     |      |
| CTT | CAT | GTC | CTC | TTG | ATG | ACA | TTC | TGC | CCA | GCT | GAC | CCC | TAC | TGT | GCC |     |     | 888  |
| Leu | His | Val | Leu | Leu | Met | Thr | Phe | Cys | Pro | Ala | Asp | Pro | Tyr | Cys | Ala |     |     |      |
|     |     |     | 240 |     |     |     |     | 245 |     |     |     |     | 250 |     |     |     |     |      |
| TGC | TAC | ATG | TCC | CTC | TTC | CAG | GTG | AAT | GGT | GTG | TTG | ATC | ATG | TGT | AAT |     |     | 936  |
| Cys | Tyr | Met | Ser | Leu | Phe | Gln | Val | Asn | Gly | Val | Leu | Ile | Met | Cys | Asn |     |     |      |
|     |     | 255 |     |     |     |     | 260 |     |     |     |     | 265 |     |     |     |     |     |      |
| GCC | ATC | ATC | GAC | CCC | TTC | ATA | TAT | GCC | TTT | CGG | AGC | CCA | GAG | CTC | AGG |     |     | 984  |
| Ala | Ile | Ile | Asp | Pro | Phe | Ile | Tyr | Ala | Phe | Arg | Ser | Pro | Glu | Leu | Arg |     |     |      |
|     | 270 |     |     |     |     | 275 |     |     |     |     | 280 |     |     |     |     |     |     |      |
| GTC | GCA | TTC | AAA | AAG | ATG | GTT | ATC | TGC | AAC | TGT | TAC | CAG | TAGAATGATT |  |  |  |  | 1033 |
| Val | Ala | Phe | Lys | Lys | Met | Val | Ile | Cys | Asn | Cys | Tyr | Gln |     |     |     |     |     |      |
| 285 |     |     |     |     | 290 |     |     |     |     | 295 |     |     |     |     |     |     |     |      |

GGTCCCTGAT TTTAGGAGCC ACAGGGATAT ACTGTCAGGG ACAGAGTAGC GTGACAGACC        1093

AACAACACTA GGACT                                                                 1108

( 2 ) INFORMATION FOR SEQ ID NO:6:

( i ) SEQUENCE CHARACTERISTICS:
        ( A ) LENGTH: 297 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Lys | His | Ile | Leu | Asn | Leu | Tyr | Glu | Asn | Ile | Asn | Ser | Thr | Ala | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asn | Asn | Ser | Asp | Cys | Pro | Ala | Val | Ile | Leu | Pro | Glu | Glu | Ile | Phe | Phe |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

-continued

| | | | | | | | | | | | | | | | |
|---|---|---|---|---|---|---|---|---|---|---|---|---|---|---|---|
| Thr | Val | Ser<br>35 | Ile | Val | Gly | Val | Leu<br>40 | Glu | Asn | Leu | Met | Val<br>45 | Leu | Leu | Ala |
| Val | Ala<br>50 | Lys | Asn | Lys | Ser | Leu<br>55 | Gln | Ser | Pro | Met | Tyr<br>60 | Phe | Phe | Ile | Cys |
| Ser<br>65 | Leu | Ala | Ile | Ser | Asp<br>70 | Met | Leu | Gly | Ser | Leu<br>75 | Tyr | Lys | Ile | Leu | Glu<br>80 |
| Asn | Val | Leu | Ile | Met<br>85 | Phe | Lys | Asn | Met | Gly<br>90 | Tyr | Leu | Glu | Pro | Arg<br>95 | Gly |
| Ser | Phe | Glu | Ser<br>100 | Thr | Ala | Asp | Asp | Val<br>105 | Val | Asp | Ser | Leu | Phe<br>110 | Ile | Leu |
| Ser | Leu | Leu<br>115 | Gly | Ser | Ile | Cys | Ser<br>120 | Leu | Ser | Val | Ile | Ala<br>125 | Ala | Asp | Arg |
| Tyr | Ile<br>130 | Thr | Ile | Phe | His | Ala<br>135 | Leu | Gln | Tyr | His | Arg<br>140 | Ile | Met | Thr | Pro |
| Ala<br>145 | Pro | Cys | Pro | Arg | His<br>150 | Leu | Thr | Val | Leu | Trp<br>155 | Ala | Gly | Cys | Thr | Gly<br>160 |
| Ser | Gly | Ile | Thr | Ile<br>165 | Val | Thr | Phe | Ser | His<br>170 | His | Val | Pro | Thr | Val<br>175 | Ile |
| Ala | Phe | Thr | Ala<br>180 | Leu | Phe | Pro | Leu | Met<br>185 | Leu | Ala | Phe | Ile | Leu<br>190 | Cys | Leu |
| Tyr | Val | His<br>195 | Met | Phe | Leu | Leu | Ala<br>200 | Arg | Ser | His | Thr | Arg<br>205 | Arg | Thr | Pro |
| Ser | Leu<br>210 | Pro | Lys | Ala | Asn | Met<br>215 | Arg | Gly | Ala | Val | Thr<br>220 | Leu | Thr | Val | Leu |
| Leu<br>225 | Gly | Val | Phe | Ile | Phe<br>230 | Cys | Trp | Ala | Pro | Phe<br>235 | Val | Leu | His | Val | Leu<br>240 |
| Leu | Met | Thr | Phe | Cys<br>245 | Pro | Ala | Asp | Pro | Tyr<br>250 | Cys | Ala | Cys | Tyr | Met<br>255 | Ser |
| Leu | Phe | Gln | Val<br>260 | Asn | Gly | Val | Leu | Ile<br>265 | Met | Cys | Asn | Ala | Ile<br>270 | Ile | Asp |
| Pro | Phe | Ile<br>275 | Tyr | Ala | Phe | Arg | Ser<br>280 | Pro | Glu | Leu | Arg | Val<br>285 | Ala | Phe | Lys |
| Lys | Met<br>290 | Val | Ile | Cys | Asn | Cys<br>295 | Tyr | Gln | | | | | | | |

What we claim is:

1. A method of screening a compound as an inhibitor of agonist binding to a mammalian adrenocorticotropic hormone receptor, the method comprising the following steps:
   (a) transforming a eukaryotic cell culture with an expression construct comprising a nucleotide sequence encoding a mammalian adrenocorticotropic hormone receptor having an amino acid sequence identified as SEQ ID NO:4 or SEQ ID NO:6, said construct being capable of expressing the adrenocorticotropic hormone receptor in a eukaryotic cell;
   (b) obtaining a membrane preparation from the transformed cells;
   (c) contacting the membrane preparations with the compound and a detectably labeled adrenocorticotropic hormone receptor agonist; and
   (d) assaying for ability of the compound to inhibit the binding of the detectably-labeled adrenocorticotropic hormone receptor agonist.

2. The method of claim 1 wherein the mammalian adrenocorticotropic hormone receptor is the bovine adrenocorticotropic hormone receptor.

3. The method of claim 1 wherein the mammalian adrenocorticotropic hormone receptor is the human adrenocorticotropic hormone receptor.

4. A method of assaying a compound to quantitatively characterize the compound as an inhibitor of agonist binding to a mammalian adrenocorticotropic hormone receptor, the method comprising the following steps:
   (a) transforming a eukaryotic cell culture with an expression construct comprising a nucleotide sequence encoding a mammalian adrenocorticotropic hormone receptor having an amino acid sequence identified as SEQ ID NO:4 or SEQ ID NO:6, said construct being capable of expressing the adrenocorticotropic hormone receptor in a eukaryotic cell;
   (b) obtaining a membrane preparation from the transformed cells;
   (c) contacting the membrane preparations with the compound and a detectably labeled adrenocorticotropic hormone receptor agonist; and
   (d) assaying for amount of a compound by measuring the extent of inhibition of binding of a detectably labeled adrenocorticotropic hormone receptor agonist.

5. The method of claim 4 wherein the mammalian adrenocorticotropic hormone receptor is the bovine adrenocorticotropic hormone receptor.

6. The method of claim 4 wherein the mammalian adrenocorticotropic hormone receptor is the human adrenocorticotropic hormone receptor.

7. The method of claim 4 wherein the compound to be tested is present in a human.

8. The method of claim 4 wherein the compound is present in human blood.

9. The method of claim 4 wherein the compound is present in human cerebrospinal fluid.

10. The method of claim 4 wherein the compound is unknown.

* * * * *